(12) United States Patent
Raichelgauz et al.

(10) Patent No.: US 9,747,420 B2
(45) Date of Patent: Aug. 29, 2017

(54) SYSTEM AND METHOD FOR DIAGNOSING A PATIENT BASED ON AN ANALYSIS OF MULTIMEDIA CONTENT

(71) Applicant: Cortica, Ltd., Ramat Gan (IL)

(72) Inventors: Igal Raichelgauz, New York, NY (US); Karina Odinaev, New York, NY (US); Yehoshua Y. Zeevi, Haifa (IL)

(73) Assignee: Cortica, Ltd., Tel Aviv (IL)

( * ) Notice: Subject to any disclaimer, the term of this patent is extended or adjusted under 35 U.S.C. 154(b) by 363 days.

(21) Appl. No.: 14/314,567

(22) Filed: Jun. 25, 2014

(65) Prior Publication Data

US 2014/0310020 A1 Oct. 16, 2014

Related U.S. Application Data

(63) Continuation-in-part of application No. 13/624,397, filed on Sep. 21, 2012, now Pat. No. 9,191,626, which
(Continued)

(30) Foreign Application Priority Data

Oct. 26, 2005 (IL) .......................................... 171577
Jan. 29, 2006 (IL) .......................................... 173409
Aug. 21, 2007 (IL) .......................................... 185414

(51) Int. Cl.
*G06F 19/00* (2011.01)
*H04N 7/173* (2011.01)
(Continued)

(52) U.S. Cl.
CPC .......... *G06F 19/345* (2013.01); *G06T 7/0014* (2013.01); *H04N 7/17318* (2013.01);
(Continued)

(58) Field of Classification Search
None
See application file for complete search history.

(56) References Cited

U.S. PATENT DOCUMENTS 4,733,353 A 3/1988 Jaswa
4,932,645 A 6/1990 Schorey et al.
(Continued)

FOREIGN PATENT DOCUMENTS

WO 0231764 4/2002
WO 03005242 A1 1/2003
(Continued)

OTHER PUBLICATIONS

Boari et al, "Adaptive Routing for Dynamic Applications in Massively Parallel Architectures", 1995 IEEE, Spring 1995.
(Continued)

*Primary Examiner* — Alan Chen
(74) *Attorney, Agent, or Firm* — M&B IP Analysts, LLC

(57) ABSTRACT

A method for diagnosing a patient based on analysis of multimedia content is provided. The method includes receiving at least one multimedia content element respective of the patient from a user device; generating at least one signature for the at least one multimedia content element; generating at least one identifier respective of the at least one multimedia content element using the at least one generated signature; searching a plurality of data sources for possible diagnoses respective of the one or more identifiers; and providing at least one possible diagnoses respective of the at least one multimedia content element to the user device.

20 Claims, 5 Drawing Sheets

Related U.S. Application Data is a continuation-in-part of application No. 13/344,400, filed on Jan. 5, 2012, now Pat. No. 8,959,037, which is a continuation of application No. 12/434,221, filed on May 1, 2009, now Pat. No. 8,112,376, said application No. 13/624,397 is a continuation-in-part of application No. 12/195,863, filed on Aug. 21, 2008, now Pat. No. 8,326,775, which is a continuation-in-part of application No. 12/084,150, filed as application No. PCT/IL2006/001235 on Oct. 26, 2006, now Pat. No. 8,655,801.

(60) Provisional application No. 61/839,871, filed on Jun. 27, 2013.

(51) Int. Cl.
  *H04N 21/258* (2011.01)
  *H04N 21/2668* (2011.01)
  *H04N 21/466* (2011.01)
  *H04N 21/81* (2011.01)
  *G06T 7/00* (2017.01)

(52) U.S. Cl.
  CPC ... *H04N 21/25891* (2013.01); *H04N 21/2668* (2013.01); *H04N 21/466* (2013.01); *H04N 21/8106* (2013.01); *G06T 2207/10016* (2013.01); *G06T 2207/10024* (2013.01); *G06T 2207/30088* (2013.01)

(56) References Cited

U.S. PATENT DOCUMENTS

| | | |
|---|---|---|
| 4,972,363 A | 11/1990 | Nguyen et al. |
| 5,307,451 A | 4/1994 | Clark |
| 5,568,181 A | 10/1996 | Greenwood et al. |
| 5,806,061 A | 9/1998 | Chaudhuri et al. |
| 5,852,435 A | 12/1998 | Vigneaux et al. |
| 5,870,754 A | 2/1999 | Dimitrova et al. |
| 5,873,080 A | 2/1999 | Coden et al. |
| 5,940,821 A | 8/1999 | Wical |
| 5,987,454 A | 11/1999 | Hobbs |
| 6,038,560 A | 3/2000 | Wical |
| 6,122,628 A | 9/2000 | Castelli et al. |
| 6,128,651 A | 10/2000 | Cezar |
| 6,137,911 A | 10/2000 | Zhilyaev |
| 6,144,767 A | 11/2000 | Bottou et al. |
| 6,173,068 B1 * | 1/2001 | Prokoski ............... A61B 5/015 382/115 |
| 6,240,423 B1 | 5/2001 | Hirata |
| 6,243,375 B1 | 6/2001 | Speicher |
| 6,243,713 B1 | 6/2001 | Nelson et al. |
| 6,329,986 B1 | 12/2001 | Cheng |
| 6,363,373 B1 | 3/2002 | Steinkraus |
| 6,381,656 B1 | 4/2002 | Shankman |
| 6,493,692 B1 | 12/2002 | Kobayashi et al. |
| 6,493,705 B1 | 12/2002 | Kobayashi et al. |
| 6,523,022 B1 | 2/2003 | Hobbs |
| 6,523,046 B2 | 2/2003 | Liu et al. |
| 6,526,400 B1 | 2/2003 | Takata et al. |
| 6,550,018 B1 | 4/2003 | Abonamah et al. |
| 6,560,597 B1 | 5/2003 | Dhillon et al. |
| 6,594,699 B1 | 7/2003 | Sahai et al. |
| 6,601,060 B1 | 7/2003 | Tomaru |
| 6,611,628 B1 | 8/2003 | Sekiguchi et al. |
| 6,611,837 B2 | 8/2003 | Schreiber |
| 6,618,711 B1 | 9/2003 | Ananth |
| 6,665,657 B1 | 12/2003 | Dibachi |
| 6,675,159 B1 | 1/2004 | Lin et al. |
| 6,704,725 B1 | 3/2004 | Lee |
| 6,728,706 B2 | 4/2004 | Aggarwal et al. |
| 6,732,149 B1 | 5/2004 | Kephart |
| 6,751,613 B1 | 6/2004 | Lee et al. |
| 6,754,435 B2 | 6/2004 | Kim |
| 6,774,917 B1 | 8/2004 | Foote et al. |
| 6,795,818 B1 | 9/2004 | Lee |
| 6,819,797 B1 | 11/2004 | Smith et al. |
| 6,836,776 B2 | 12/2004 | Schreiber |
| 6,901,207 B1 | 5/2005 | Watkins |
| 6,938,025 B1 | 8/2005 | Lulich et al. |
| 6,970,881 B1 | 11/2005 | Mohan et al. |
| 6,978,264 B2 | 12/2005 | Chandrasekar et al. |
| 7,013,051 B2 | 3/2006 | Sekiguchi et al. |
| 7,020,654 B1 | 3/2006 | Najmi |
| 7,047,033 B2 | 5/2006 | Wyler |
| 7,124,149 B2 | 10/2006 | Smith et al. |
| 7,199,798 B1 | 4/2007 | Echigo et al. |
| 7,260,564 B1 | 8/2007 | Lynn et al. |
| 7,277,928 B2 | 10/2007 | Lennon |
| 7,296,012 B2 | 11/2007 | Ohashi |
| 7,302,117 B2 | 11/2007 | Sekiguchi et al. |
| 7,313,805 B1 | 12/2007 | Rosin et al. |
| 7,340,458 B2 | 3/2008 | Vaithilingam et al. |
| 7,346,629 B2 | 3/2008 | Kapur et al. |
| 7,353,224 B2 | 4/2008 | Chen et al. |
| 7,376,672 B2 | 5/2008 | Weare |
| 7,376,722 B1 | 5/2008 | Sim et al. |
| 7,392,238 B1 | 6/2008 | Zhou et al. |
| 7,406,459 B2 | 7/2008 | Chen et al. |
| 7,433,895 B2 | 10/2008 | Li et al. |
| 7,450,740 B2 | 11/2008 | Shah et al. |
| 7,464,086 B2 | 12/2008 | Black et al. |
| 7,523,102 B2 | 4/2009 | Bjarnestam et al. |
| 7,526,607 B1 | 4/2009 | Singh et al. |
| 7,536,384 B2 | 5/2009 | Venkataraman et al. |
| 7,536,417 B2 | 5/2009 | Walsh et al. |
| 7,542,969 B1 | 6/2009 | Rappaport et al. |
| 7,548,910 B1 | 6/2009 | Chu et al. |
| 7,555,477 B2 | 6/2009 | Bayley et al. |
| 7,555,478 B2 | 6/2009 | Bayley et al. |
| 7,562,076 B2 | 7/2009 | Kapur |
| 7,574,436 B2 | 8/2009 | Kapur et al. |
| 7,574,668 B2 | 8/2009 | Nunez et al. |
| 7,657,100 B2 | 2/2010 | Gokturk et al. |
| 7,660,468 B2 | 2/2010 | Gokturk et al. |
| 7,660,737 B1 | 2/2010 | Lim et al. |
| 7,697,791 B1 | 4/2010 | Chan et al. |
| 7,769,221 B1 | 8/2010 | Shakes et al. |
| 7,788,132 B2 | 8/2010 | Desikan et al. |
| 7,860,895 B1 | 12/2010 | Scofield et al. |
| 7,904,503 B2 | 3/2011 | Van De Sluis |
| 7,920,894 B2 | 4/2011 | Wyler |
| 7,921,107 B2 | 4/2011 | Chang et al. |
| 7,974,994 B2 | 7/2011 | Li et al. |
| 7,987,194 B1 | 7/2011 | Walker et al. |
| 7,987,217 B2 | 7/2011 | Long et al. |
| 7,991,715 B2 | 8/2011 | Schiff et al. |
| 8,000,655 B2 | 8/2011 | Wang et al. |
| 8,112,376 B2 | 2/2012 | Raichelgauz et al. |
| 8,315,442 B2 | 11/2012 | Gokturk et al. |
| 8,316,005 B2 | 11/2012 | Moore |
| 8,326,775 B2 | 12/2012 | Raichelgauz et al. |
| 8,345,982 B2 | 1/2013 | Gokturk et al. |
| 8,548,828 B1 * | 10/2013 | Longmire ............... G06Q 10/10 705/3 |
| 8,655,801 B2 | 2/2014 | Raichelgauz et al. |
| 8,799,195 B2 | 8/2014 | Raichelgauz et al. |
| 8,799,196 B2 | 8/2014 | Raichelquaz et al. |
| 8,818,916 B2 | 8/2014 | Raichelgauz et al. |
| 8,886,648 B1 | 11/2014 | Procopio et al. |
| 9,330,189 B2 | 5/2016 | Raichelgauz et al. |
| 9,438,270 B2 | 9/2016 | Raichelgauz et al. |
| 2001/0019633 A1 | 9/2001 | Tenze et al. |
| 2002/0019881 A1 | 2/2002 | Bokhari et al. |
| 2002/0038299 A1 | 3/2002 | Zernik et al. |
| 2002/0059580 A1 | 5/2002 | Kalker et al. |
| 2002/0099870 A1 | 7/2002 | Miller et al. |
| 2002/0123928 A1 | 9/2002 | Eldering et al. |
| 2002/0129296 A1 | 9/2002 | Kwiat et al. |
| 2002/0152267 A1 | 10/2002 | Lennon |
| 2002/0157116 A1 | 10/2002 | Jasinschi |
| 2002/0159640 A1 | 10/2002 | Vaithilingam et al. |
| 2002/0161739 A1 | 10/2002 | Oh |

(56) References Cited

U.S. PATENT DOCUMENTS

| | | |
|---|---|---|
| 2002/0163532 A1 | 11/2002 | Thomas et al. |
| 2002/0174095 A1 | 11/2002 | Lulich et al. |
| 2003/0041047 A1 | 2/2003 | Chang et al. |
| 2003/0050815 A1 | 3/2003 | Seigel et al. |
| 2003/0086627 A1 | 5/2003 | Berriss et al. |
| 2003/0200217 A1 | 10/2003 | Ackerman |
| 2003/0217335 A1 | 11/2003 | Chung et al. |
| 2004/0003394 A1 | 1/2004 | Ramaswamy |
| 2004/0025180 A1 | 2/2004 | Begeja et al. |
| 2004/0117367 A1 | 6/2004 | Smith et al. |
| 2004/0133927 A1 | 7/2004 | Sternberg et al. |
| 2004/0153426 A1 | 8/2004 | Nugent |
| 2004/0215663 A1 | 10/2004 | Liu et al. |
| 2004/0260688 A1 | 12/2004 | Gross |
| 2004/0267774 A1 | 12/2004 | Lin et al. |
| 2005/0131884 A1 | 6/2005 | Gross et al. |
| 2005/0177372 A1 | 8/2005 | Wang et al. |
| 2005/0238238 A1 | 10/2005 | Xu et al. |
| 2005/0245241 A1 | 11/2005 | Durand et al. |
| 2005/0281439 A1 | 12/2005 | Lange |
| 2006/0004745 A1 | 1/2006 | Kuhn et al. |
| 2006/0020958 A1 | 1/2006 | Allamanche et al. |
| 2006/0031216 A1 | 2/2006 | Semple et al. |
| 2006/0041596 A1 | 2/2006 | Stirbu et al. |
| 2006/0048191 A1 | 3/2006 | Xiong |
| 2006/0112035 A1 | 5/2006 | Cecchi et al. |
| 2006/0129822 A1 | 6/2006 | Snijder et al. |
| 2006/0153296 A1 | 7/2006 | Deng |
| 2006/0184638 A1 | 8/2006 | Chua et al. |
| 2006/0217818 A1 | 9/2006 | Fujiwara |
| 2006/0224529 A1 | 10/2006 | Kermani |
| 2006/0236343 A1 | 10/2006 | Chang |
| 2006/0242554 A1 | 10/2006 | Gerace et al. |
| 2006/0247983 A1 | 11/2006 | Dalli |
| 2006/0248558 A1 | 11/2006 | Barton et al. |
| 2006/0253423 A1 | 11/2006 | McLane et al. |
| 2007/0009159 A1 | 1/2007 | Fan |
| 2007/0011151 A1 | 1/2007 | Hagar et al. |
| 2007/0019864 A1 | 1/2007 | Koyama et al. |
| 2007/0038608 A1 | 2/2007 | Chen |
| 2007/0061302 A1 | 3/2007 | Ramer et al. |
| 2007/0067304 A1 | 3/2007 | Ives |
| 2007/0074147 A1 | 3/2007 | Wold |
| 2007/0091106 A1 | 4/2007 | Moroney |
| 2007/0130112 A1 | 6/2007 | Lin |
| 2007/0130159 A1 | 6/2007 | Gulli et al. |
| 2007/0168413 A1 | 7/2007 | Barletta et al. |
| 2007/0174320 A1 | 7/2007 | Chou |
| 2007/0195987 A1 | 8/2007 | Rhoads |
| 2007/0220573 A1 | 9/2007 | Chiussi et al. |
| 2007/0244902 A1 | 10/2007 | Seide et al. |
| 2007/0253594 A1 | 11/2007 | Lu et al. |
| 2007/0255785 A1 | 11/2007 | Hayashi et al. |
| 2007/0268309 A1 | 11/2007 | Tanigawa et al. |
| 2007/0282826 A1 | 12/2007 | Hoeber et al. |
| 2007/0294295 A1 | 12/2007 | Finkelstein et al. |
| 2008/0040277 A1 | 2/2008 | DeWitt |
| 2008/0046406 A1 | 2/2008 | Seide et al. |
| 2008/0049629 A1 | 2/2008 | Morrill |
| 2008/0072256 A1 | 3/2008 | Boicey et al. |
| 2008/0152231 A1 | 6/2008 | Gokturk et al. |
| 2008/0163288 A1 | 7/2008 | Ghosal et al. |
| 2008/0172615 A1 | 7/2008 | Igelman et al. |
| 2008/0201299 A1 | 8/2008 | Lehikoinen et al. |
| 2008/0201314 A1 | 8/2008 | Smith et al. |
| 2008/0204706 A1 | 8/2008 | Magne et al. |
| 2008/0313140 A1 | 12/2008 | Pereira et al. |
| 2009/0022472 A1 | 1/2009 | Bronstein et al. |
| 2009/0037408 A1 | 2/2009 | Rodgers |
| 2009/0089587 A1 | 4/2009 | Brunk et al. |
| 2009/0125529 A1 | 5/2009 | Vydiswaran et al. |
| 2009/0125544 A1 | 5/2009 | Brindley |
| 2009/0148045 A1 | 6/2009 | Lee et al. |
| 2009/0157575 A1 | 6/2009 | Schobben et al. |
| 2009/0172030 A1 | 7/2009 | Schiff et al. |
| 2009/0204511 A1 | 8/2009 | Tsang |
| 2009/0216639 A1 | 8/2009 | Kapczynski et al. |
| 2009/0245603 A1 | 10/2009 | Koruga et al. |
| 2009/0253583 A1 | 10/2009 | Yoganathan |
| 2010/0023400 A1 | 1/2010 | DeWitt |
| 2010/0088321 A1 | 4/2010 | Solomon et al. |
| 2010/0106857 A1 | 4/2010 | Wyler |
| 2010/0125569 A1 | 5/2010 | Nair et al. |
| 2010/0191567 A1 | 7/2010 | Lee et al. |
| 2010/0318493 A1 | 12/2010 | Wessling |
| 2010/0322522 A1 | 12/2010 | Wang et al. |
| 2011/0035289 A1 | 2/2011 | King et al. |
| 2011/0106782 A1 | 5/2011 | Ke et al. |
| 2011/0145068 A1 | 6/2011 | King et al. |
| 2011/0202848 A1 | 8/2011 | Ismalon |
| 2011/0208822 A1 | 8/2011 | Rathod |
| 2012/0082362 A1* | 4/2012 | Diem .................. A61B 5/0071 382/133 |
| 2012/0150890 A1 | 6/2012 | Jeong et al. |
| 2013/0089248 A1* | 4/2013 | Remiszewski ..... G06K 9/00127 382/128 |
| 2013/0104251 A1 | 4/2013 | Moore et al. |
| 2013/0159298 A1 | 6/2013 | Mason et al. |
| 2013/0173635 A1 | 7/2013 | Sanjeev |
| 2014/0176604 A1 | 6/2014 | Venkitaraman et al. |
| 2014/0188786 A1 | 7/2014 | Raichelgauz et al. |
| 2014/0226900 A1* | 8/2014 | Saban .................. G06T 7/0081 382/165 |
| 2014/0310825 A1 | 10/2014 | Raichelgauz et al. |

FOREIGN PATENT DOCUMENTS

| | | |
|---|---|---|
| WO | 2004019527 A1 | 3/2004 |
| WO | 2007049282 | 5/2007 |
| WO | 2014137337 A1 | 9/2014 |
| WO | 2016040376 A1 | 3/2016 |

OTHER PUBLICATIONS

Cococcioni, et al, "Automatic Diagnosis of Defects of Rolling Element Bearings Based on Computational Intelligence Techniques", University of Pisa, Pisa, Italy, 2009.

Emami, et al, "Role of Spatiotemporal Oriented Energy Features for Robust Visual Tracking in Video Surveillance, University of Queensland", St. Lucia, Australia, 2012.

Garcia, "Solving the Weighted Region Least Cost Path Problem Using Transputers", Naval Postgraduate School, Monterey, California, Dec. 1989.

Mahdhaoui, et al, "Emotional Speech Characterization Based on Multi-Features Fusion for Face-to-Face Interaction", Universite Pierre et Marie Curie, Paris, France, 2009.

Marti, et al, "Real Time Speaker Localization and Detection System for Camera Steering in Multiparticipant Videoconferencing Environments", Universidad Politecnica de Valencia, Spain, 2011.

Nagy et al, "A Transputer, Based, Flexible, Real-Time Control System for Robotic Manipulators", UKACC International Conference on Control '96, Sep. 2-5, 1996, Conference 1996, Conference Publication No. 427, IEE 1996.

Scheper, et al. "Nonlinear dynamics in neural computation", ESANN'2006 proceedings—European Symposium on Artificial Neural Networks, Bruges (Belgium), Apr. 26-28, 2006, d-side publi, ISBN 2-930307-06-4.

Theodoropoulos et al, "Simulating Asynchronous Architectures on Transputer Networks", Proceedings of the Fourth Euromicro Workshop on Parallel and Distributed Processing, 1996. PDP '96.

Burgsteiner et al.: "Movement Prediction From Real-World Images Using a Liquid State Machine", Innovations in Applied Artificial Intelligence Lecture Notes in Computer Science, Lecture Notes in Artificial Intelligence, LNCS, Springer-Verlag, BE, vol. 3533, Jun. 2005, pp. 121-130.

Cernansky et al., "Feed-forward Echo State Networks"; Proceedings of International Joint Conference on Neural Networks, Montreal, Canada, Jul. 31-Aug. 4, 2005.

(56) References Cited

OTHER PUBLICATIONS

Fathy et al., "A Parallel Design and Implementation for Backpropagation Neural Network Using NIMD Architecture", 8th Mediterranean Electrotechnical Corsfe rersce, 19'96. MELECON '96, Date of Conference: May 13-16, 1996, vol. 3, pp. 1472-1475.
Foote, Jonathan et al., "Content-Based Retrieval of Music and Audio", 1997, Institute of Systems Science, National University of Singapore, Singapore (Abstract).
Freisleben et al., "Recognition of Fractal Images Using a Neural Network", Lecture Notes in Computer Science, 1993, vol. 6861, 1993, pp. 631-637.
Howlett et al., "A Multi-Computer Neural Network Architecture in a Virtual Sensor System Application", International Journal of Knowledge-based Intelligent Engineering Systems, 4 (2). pp. 86-93, 133N 1327-2314; first submitted Nov. 30, 1999; revised version submitted Mar. 10, 2000.
International Search Authority: "Written Opinion of the International Searching Authority" (PCT Rule 43bis.1) including International Search Report for International Patent Application No. PCT/US2008/073852; Date of Mailing: Jan. 28, 2009.
International Search Authority: International Preliminary Report on Patentability (Chapter I of the Patent Cooperation Treaty) including "Written Opinion of the International Searching Authority" (PCT Rule 43bis. 1) for the corresponding International Patent Application No. PCT/IL2006/001235; Date of Issuance: Jul. 28, 2009.
International Search Report for the corresponding International Patent Application PCT/IL2006/001235; Date of Mailing: Nov. 2, 2008.
IPO Examination Report under Section 18(3) for corresponding UK application No. GB1001219.3, dated Sep. 12, 2011; Entire Document.
Iwamoto, K.; Kasutani, E.; Yamada, A.: "Image Signature Robust to Caption Superimposition for Video Sequence Identification"; 2006 IEEE International Conference on Image Processing; pp. 3185-3188, Oct. 8-11, 2006; doi: 10.1109/ICIP.2006.313046.
Jaeger, H.: "The "echo state" approach to analysing and training recurrent neural networks", GMD Report, No. 148, 2001, pp. 1-43, XP002466251. German National Research Center for Information Technology.
Lin, C.; Chang, S.: "Generating Robust Digital Signature for Image/Video Authentication", Multimedia and Security Workshop at ACM Mutlimedia '98; Bristol, U.K., Sep. 1998; pp. 49-54.
Lyon, Richard F.; "Computational Models of Neural Auditory Processing"; IEEE International Conference on Acoustics, Speech, and Signal Processing, ICASSP '84, Date of Conference: Mar. 1984, vol. 9, pp. 41-44.
Maass, W. et al.: "Computational Models for Generic Cortical Microcircuits", Institute for Theoretical Computer Science, Technische Universitaet Graz, Graz, Austria, published Jun. 10, 2003.
Morad, T.Y. et al.: "Performance, Power Efficiency and Scalability of Asymmetric Cluster Chip Multiprocessors", Computer Architecture Letters, vol. 4, Jul. 4, 2005 (Jul. 4, 2005), pp. 1-4, XP002466254.
Natsclager, T. et al.: "The "liquid computer": A novel strategy for real-time computing on time series", Special Issue on Foundations of Information Processing of Telematik, vol. 8, No. 1, 2002, pp. 39-43, XP002466253.
Ortiz-Boyer et al., "CIXL2: A Crossover Operator for Evolutionary Algorithms Based on Population Features", Journal of Artificial Intelligence Research 24 (2005) 1-48 Submitted Nov. 2004; published Jul. 2005.
Raichelgauz, I. et al.: "Co-evolutionary Learning in Liquid Architectures", Lecture Notes in Computer Science, [Online] vol. 3512, Jun. 21, 2005 (Jun. 21, 2005), pp. 241-248, XP019010280 Springer Berlin / Heidelberg ISSN: 1611-3349 ISBN: 978-3-540-26208-4.
Ribert et al. "An Incremental Hierarchical Clustering", Visicon Interface 1999, pp. 586-591.
Verstraeten et al., "Isolated word recognition with the Liquid State Machine: a case study"; Department of Electronics and Information Systems, Ghent University, Sint-Pietersnieuwstraat 41, 9000 Gent, Belgium, Available online Jul. 14, 2005.
Verstraeten et al.: "Isolated word recognition with the Liquid State Machine: a case study", Information Processing Letters, Amsterdam, NL, vol. 95, No. 6, Sep. 20, 2005 (Sep. 30, 2005), pp. 521-528, XP005028093 ISSN: 0020-0190.
Ware et al., "Locating and Identifying Components in a Robot's Workspace using a Hybrid Computer Architecture"; Proceedings of the 1995 IEEE International Symposium on Intelligent Control, Aug. 27-29, 1995, pp. 139-144.
Xian-Sheng Hua et al.: "Robust Video Signature Based on Ordinal Measure" In: 2004 International Conference on Image Processing, ICIP '04; Microsoft Research Asia, Beijing, China; published Oct. 24-27, 2004, pp. 685-688.
Zeevi, Y. et al.: "Natural Signal Classification by Neural Cliques and Phase-Locked Attractors", IEEE World Congress on Computational Intelligence, IJCNN2006, Vancouver, Canada, Jul. 2006 (Jul. 2006), XP002466252.
Zhou et al., "Ensembling neural networks: Many could be better than all"; National Laboratory for Novel Software Technology, Nanjing Unviersirty, Hankou Road 22, Nanjing 210093, PR China; Available online Mar. 12, 2002.
Zhou et al., "Medical Diagnosis With C4.5 Rule Preceded by Artificial Neural Network Ensemble"; IEEE Transactions on Information Technology in Biomedicine, vol. 7, Issue: 1, pp. 37-42, Date of Publication: Mar. 2003.
Chuan-Yu Cho, et al., "Efficient Motion-Vector-Based Video Search Using Query by Clip", 2004, IEEE, Taiwan, pp. 1-4.
Ihab Al Kabary, et al., "SportSense: Using Motion Queries to Find Scenes in Sports Videos", Oct. 2013, ACM, Switzerland, pp. 1-3.
Jianping Fan et al., "Concept-Oriented Indexing of Video Databases: Towards Semantic Sensitive Retrieval and Browsing", IEEE, vol. 13, No. 7, Jul. 2004, pp. 1-19.
Shih-Fu Chang, et al., "VideoQ: A Fully Automated Video Retrieval System Using Motion Sketches", 1998, IEEE, , New York, pp. 1-2.
Wei-Te Li et al., "Exploring Visual and Motion Saliency for Automatic Video Object Extraction", IEEE, vol. 22, No. 7, Jul. 2013, pp. 1-11.
Brecheisen, et al., "Hierarchical Genre Classification for Large Music Collections", ICME 2006, pp. 1385-1388.
Lau, et al., "Semantic Web Service Adaptation Model for a Pervasive Learning Scenario", 2008 IEEE Conference on Innovative Technologies in Intelligent Systems and Industrial Applications Year: 2008, pp. 98-103, DOI: 10.1109/CITISIA.2008.4607342 IEEE Conference Publications.
McNamara, et al., "Diversity Decay in Opportunistic Content Sharing Systems", 2011 IEEE International Symposium on a World of Wireless, Mobile and Multimedia Networks Year: 2011, pp. 1-3, DOI: 10.1109/WoWMoM.2011.5986211 IEEE Conference Publications.
Santos, et al., "SCORM-MPEG: an Ontology of Interoperable Metadata for Multimedia and e-Learning", 2015 23rd International Conference on Software, Telecommunications and Computer Networks (SoftCOM) Year: 2015, pp. 224-228, DOI: 10.1109/SOFTCOM.2015.7314122 IEEE Conference Publications.
Wilk, et al., "The Potential of Social-Aware Multimedia Prefetching on Mobile Devices", 2015 International Conference and Workshops on Networked Systems (NetSys) Year: 2015, pp. 1-5, DOI: 10.1109/NetSys.2015.7089081 IEEE Conference Publications.
Odinaev, et al., "Cliques in Neural Ensembles as Perception Carriers", Technion—Israel Institute of Technology, 2006 International Joint Conference on Neural Networks, Canada, 2006, pp. 285-292.
The International Search Report and the Written Opinion for PCT/US2016/054634 dated Mar. 16, 2017, ISA/RU, Moscow, RU.

* cited by examiner

SYSTEM AND METHOD FOR DIAGNOSING A PATIENT BASED ON AN ANALYSIS OF MULTIMEDIA CONTENT

CROSS-REFERENCE TO RELATED APPLICATIONS

This application claims the benefit of U.S. Provisional Application No. 61/839,871 filed on Jun. 27, 2013. This application is also a continuation-in-part (CIP) of U.S. patent application Ser. No. 13/624,397 filed on Sep. 21, 2012. The Ser. No. 13/624,397 Application is a continuation-in-part of:
 (a) U.S. patent application Ser. No. 13/344,400 filed on Jan. 5, 2012, which is a continuation of U.S. patent application Ser. No. 12/434,221, filed May 1, 2009, now U.S. Pat. No. 8,112,376. The Ser. No. 13/344,400 Application is also a continuation-in-part of the below-referenced U.S. patent application Ser. No. 12/195,863 and Ser. No. 12/084,150;
 (b) U.S. patent application Ser. No. 12/195,863, filed Aug. 21, 2008, now U.S. Pat. No. 8,326,775, which claims priority under 35 USC 119 from Israeli Application No. 185414, filed on Aug. 21, 2007, and which is also a continuation-in-part of the below-referenced U.S. patent application Ser. No. 12/084,150; and,
 (c) U.S. patent application Ser. No. 12/084,150 filed on Apr. 7, 2009, now U.S. Pat. No. 8,655,801, which is the National Stage of International Application No. PCT/IL2006/001235, filed on Oct. 26, 2006, which claims foreign priority from Israeli Application No. 171577 filed on Oct. 26, 2005 and Israeli Application No. 173409 filed on 29 Jan. 2006.

All of the applications referenced above are herein incorporated by reference for all that they contain.

TECHNICAL FIELD

The present invention relates generally to the analysis of multimedia content, and, more specifically, to a system for diagnosing a patient based on an analysis of multimedia content.

BACKGROUND

The current methods used to diagnose a disease of a medical condition usually rely on a patient's visit to a medical professional who is specifically trained to diagnose specific medical conditions that the patient may suffer from.

Today, an abundance of data relating to such medical condition is likely to be available through various sources in general and the Internet and world-wide web (WWW) in particular. This data allows the patient, if he or she is so inclined, to at least begin to understand the medical condition by searching for information about it.

The problem is that, while a person searches through the web for a self-diagnosis, the person may ignore one or more identifiers which are related to the medical condition and, therefore, may receive information that is inappropriate or inaccurate with respect to the person's specific medical condition. This inappropriate or inaccurate information often leads to a misdiagnosis by the patient, increased anxiety, and waste of a doctor or other caregiver's time as such caregiver needs to correct the misinformed patient's understanding of the medical condition.

As an example, a person may experience a rash and look up medical conditions related to rashes. Without expertise in dermatology, the person may determine that the experienced rash is similar to that caused by poison ivy. An immediate remedy may be cleaning the rash followed by calamine lotion is the only necessary treatment. However, if the rash is caused by an allergic reaction to a food, a different treatment may be require, such as exposure to epinephrine.

Moreover, a patient may receive digital content respective of the medical condition including, but not limited to, medical reports, images, and other multimedia content. However, other than being able to send such content to other advice providers, the patients cannot typically effectively use such content to aid in diagnosis. Rather, the patient can frequently only provide the content to a caregiver or someone else who is capable of adequately understanding the relevance of such content.

It would be therefore advantageous to provide a solution for identifying a plurality of disease characteristics related to patients, and providing diagnoses respective thereof.

SUMMARY

Certain embodiments disclosed herein include a method and system for diagnosing a patient based on analysis of multimedia content. The method includes receiving at least one multimedia content element respective of the patient from a user device; generating at least one signature for the at least one multimedia content element; generating at least one identifier respective of the at least one multimedia content element using the at least one generated signature; searching a plurality of data sources for possible diagnoses respective of the one or more identifiers; and providing at least one possible diagnoses respective of the at least one multimedia content element to the user device.

BRIEF DESCRIPTION OF THE DRAWINGS

The subject matter disclosed herein is particularly pointed out and distinctly claimed in the claims at the conclusion of the specification. The foregoing and other objects, features, and advantages of the invention will be apparent from the following detailed description taken in conjunction with the accompanying drawings.

DETAILED DESCRIPTION

Figure 1:
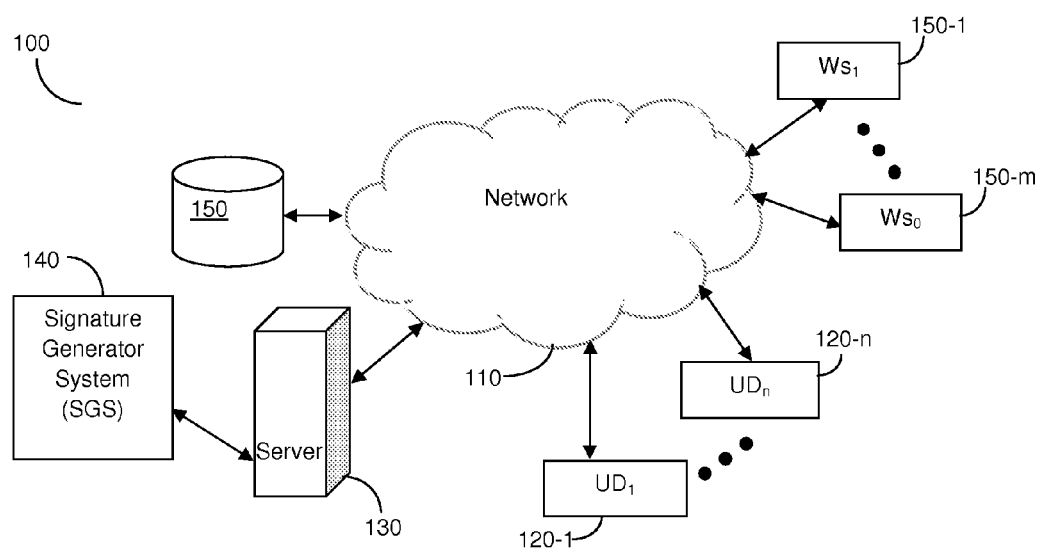
FIG. 1 is a schematic block diagram of a system for analyzing multimedia content according to one embodiment.

It is important to note that the embodiments disclosed herein are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views Certain exemplary embodiments disclosed herein enable the possible diagnosis of patients based on the analysis of multimedia content. The diagnosis may be used, for example, as a preliminary diagnostic tool by a patient or as a recommendation tool for a medical specialist. The diagnosis begins with generating signatures for the multimedia content. The generated signatures are analysis one or more identifiers related to a patient are provided. The identifiers are used in order to provide the possible diagnoses. An identifier is an element identified within the multimedia content which may be used for diagnosing the medical condition of a patient. The identifiers may be visual, for example abnormal marks on a body part or vocal, for example, hoarseness in the patient's voice. The multimedia content is analyzed and one or more matching signatures are generated respective thereto. Thereafter, the signatures generated for the identifiers are used for searching possible diagnoses through one or more data sources. The diagnoses are then provided to the user. According to another embodiment, the one or more possible diagnoses are stored in a data warehouse or a database.

As a non-limiting example, an image of a patient's face is received by a user device. One or more signatures are generated respective of the received image. An analysis of the one or more generated signatures is then performed. The analysis may include a process of matching the signatures to one or more signatures existing in a data warehouse and extraction of identifiers respective of the matching process. Identifiers may be extracted if, e.g., such identifiers are associated with signatures from the data warehouse that demonstrated matching with the one or more generated signatures. Based on the analysis of the one or more signatures, the patient is identified as an infant. In addition, abnormal skin redness is identified on the patient's face through the image.

Respective of the identifiers, a search is performed through a plurality of data sources for possible diagnoses. The search may be made by, for example, using the image as a search query as further described in U.S. patent application Ser. No. 13/773,112, assigned to common assignee, and is hereby incorporated by reference for all the useful information they contain. While searching through the plurality of data sources for a possible diagnosis, skin redness is identified as a common syndrome of the atopic dermatitis disease among infants. The possible diagnosis is then provided to the user device and then stored in a database for further use.

FIG. 1 shows an exemplary and non-limiting schematic diagram of a system 100 utilized to describe the various embodiments disclosed herein. A network 110 may be the Internet, the world-wide-web (WWW), a local area network (LAN), a wide area network (WAN), a metro area network (MAN), and other networks capable of enabling communication between the elements of the system 100.

Further connected to the network 110 are one or more user devices (UD) 120-1 through 120-$n$ (collectively referred to hereinafter as user devices 120 or individually as a user device 120). A user device 120 may be, for example, a personal computer (PC), a mobile phone, a smart phone, a tablet computer, a wearable device, and the like. The user devices 120 are configured to provide multimedia content elements to a server 130 which is also connected to the network 110.

The uploaded multimedia content can be locally saved in the user device 120 or can be captured by the user device 120. For example, the multimedia content may be an image captured by a camera installed in the user device 120, a video clip saved in the user device 120, and so on. A multimedia content may be, for example, an image, a graphic, a video stream, a video clip, an audio stream, an audio clip, a video frame, a photograph, text or image thereof, and an image of signals (e.g., spectrograms, phasograms, scalograms, etc.), and/or combinations thereof and portions thereof.

The system 100 also includes one or more web sources 150-1 through 150-$m$ (collectively referred to hereinafter as web sources 150 or individually as a web source 150) that are connected to the network 110. Each of the web sources 150 may be, for example, a web server, an application server, a data repository, a database, a professional medical database, and the like. According to one embodiment, one or more multimedia content elements of normal (or baseline) identifiers are stored in a database such as, for example, a database 160. A baseline identifier may be, for example, a clean skin image, a normal voice recording, etc. The baseline identifiers are used as references in order to identify one or more abnormal identifiers while analyzing the generated signatures of an input multimedia content.

The server 130 and a signature generator system (SGS) 140 are core to the embodiments disclosed herein. In an embodiment, the server 130 is to generate one or more identifiers, either visual or vocal, which are used to search for one or more possible diagnoses.

The SGS 140 is configured to generate a signature respective of the multimedia content elements and/or content fed by the server 130. The process of generating the signatures is explained in more detail herein below with respect to FIGS. 3 and 5. Each of the server 130 and the SGS 140 is typically comprised of a processing unit, such as a processor (not shown) that is coupled to a memory. The memory contains instructions that can be executed by the processing unit. The server 130 also includes an interface (not shown) to the network 110. One of ordinary skill in the art would readily appreciate that the server 130 and SGS 140 may have different configurations without departing from the scope of the disclosed embodiments, including an embodiment where the two units are embodied as a single unit providing the functions of both server 130 and SGS 140.

The server 130 is configured to receive at least one multimedia content element from, for example, the user device 120. The at least one multimedia content element is sent to the SGS 140. The SGS 140 is configured to generate at least one signature for the at least one multimedia content element or each portion thereof. The generated signature(s) may be robust to noise and distortions as discussed below. The generated signatures are then analyzed and one or more identifiers related to the content provided are generated.

As a non-limiting example, a user captures an image by taking a picture using a smart phone (e.g., a user device 120) and uploads the picture to a server 130. In this example, the picture features an image of the user's eye when the user is infected with pinkeye. The server 130 is configured to receive the image and send the image to an SGS 140. The SGS 140 generates a signature respective of the image.

The signature generated respective of the image is compared to signatures of baseline identifiers stored in a database 160. In this example, the signature is determined to demonstrate sufficient matching with an image of a normal (uninfected) human eye used as a normal identifier. Upon further analysis, it is determined that part of the image (namely, the color of the eye in the pinkeye image) is different and, therefore, is an abnormal identifier. Consequently, this abnormal identifier is provided to a data source so that a search may be performed. When the search has been completed, the server 130 returns the results of the search indicating that the user may have pinkeye.

The signature generated for an image or any multimedia content would enable accurate recognition of abnormal identifiers. This is because the signatures generated for the multimedia content, according to the disclosed embodiments, allow for recognition and classification of multimedia elements, such as by content-tracking, video filtering, multimedia taxonomy generation, video fingerprinting, speech-to-text, audio classification, element recognition, video/image search and any other application requiring content-based signatures generation and matching for large content volumes such as web and other large-scale databases.

Figure 2:
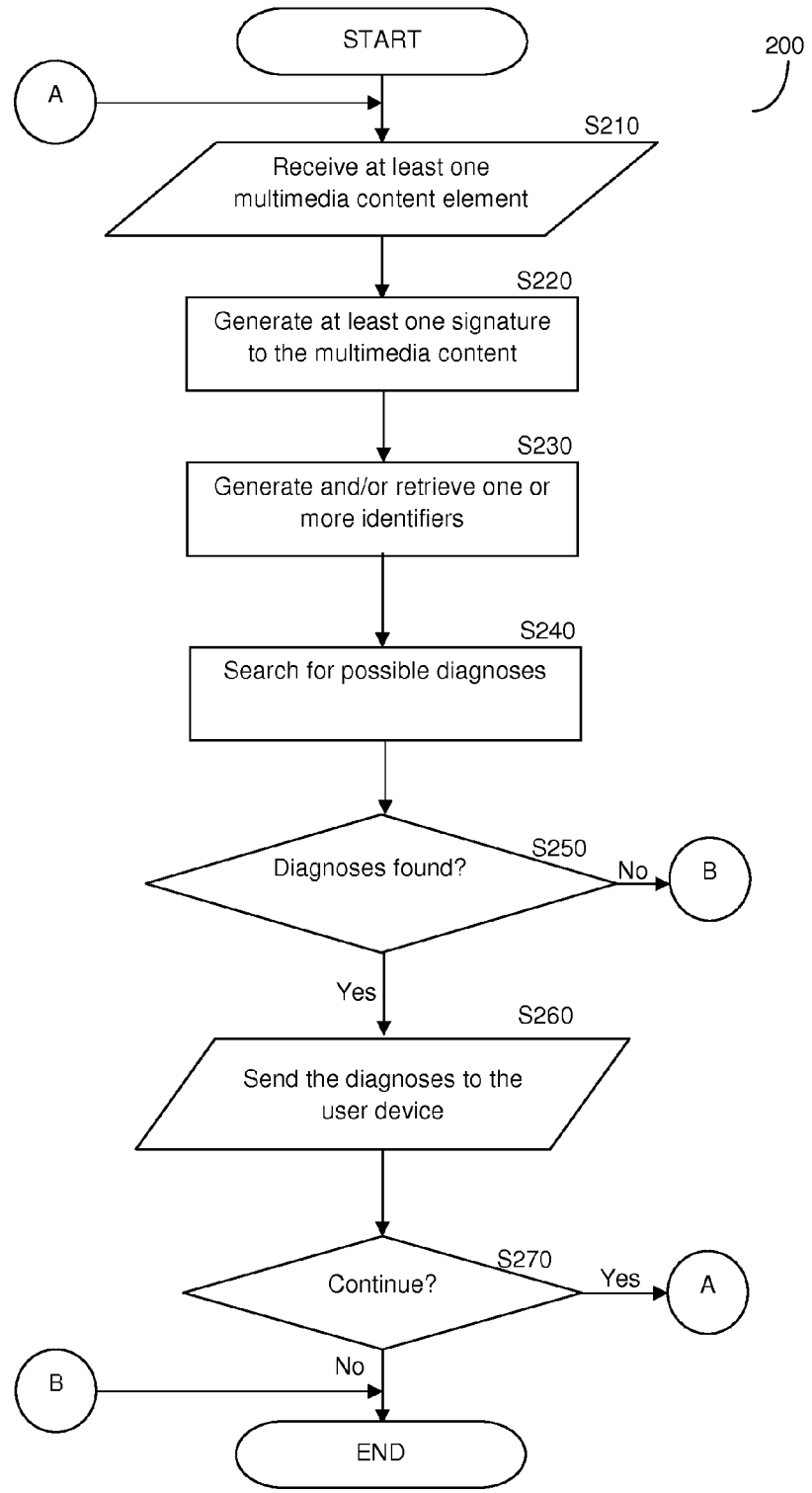
FIG. 2 is a flowchart describing a method for diagnosing a patient based on an analysis of multimedia content according to an embodiment.

FIG. 2 depicts an exemplary and non-limiting flowchart 200 describing the process of diagnosing a patient respective of an input multimedia content according to one embodiment. In S210, at least one multimedia content element is received. In an embodiment, the at least one multimedia content element may be received by, for example, any of the user devices 120. According to one embodiment, in addition to the at least one multimedia content element received, one or more metadata elements describing the patient state may be also received as an input. In S220, at least one signature is generated respective of the at least one multimedia content element. In an embodiment, the at least one signature may be generated by the SGS 140 as described below.

In S230, based on the generated signatures, at least one identifier are generated and/or retrieved. In an embodiment, the identifier(s) may be retrieved from a data warehouse (e.g., the data database 160). The identifiers may be visual or vocal. In S240, respective of the identifiers, one or more possible diagnoses are searched for through one or more data sources. The data sources may be, for example, any one of the one or more web sources 150, the database 160, and so on. According to one embodiment, the identifiers may be converted to one or more text queries which will be used in order to search for possible diagnoses through one or more search engines. In another embodiment, a signature can be generated for the identifier and the search for possible diagnoses may be performed using such signature. For example, if a redness is identified in the portion of the received multimedia content element, a signature is generated for such portion of multimedia content. The search is for possible diagnoses is performed using the signature generated for the portion of the image including the redness. Identification of diagnoses based on identifiers are discussed further herein below with respect to FIG. 5.

In S250, it is checked whether at least one possible diagnosis has been identified and, if so, execution continues with S260; otherwise, execution terminates. In S260, the one or more identified possible diagnoses are returned. According to yet another embodiment, in cases where a plurality of possible diagnosis were identified, the diagnoses may be prioritized by, for example, their commonness, the degree of match between the plurality of identifiers and the possible diagnoses, etc.

As a non-limiting example of diagnosis prioritization, if a user provides an image featuring a discoloration of the skin, the area where skin is discolored may be a visual identifier. It is determined that multiple possible diagnoses are associated with this size of skin discoloration. However, one medical condition may be identified as the highest priority diagnosis due to a high degree of matching as a result of the similarity in color between the provided discoloration and the diagnostic discoloration. As an example, an image featuring a blue discoloration may yield identification of discolorations caused by bruising as closer in color than discolorations caused by medical conditions such as eczema, chicken pox, allergic reaction, and so on, which frequently cause red discolorations. In such an example, diagnoses related to bruising (e.g., sprains, broken bones, etc.) may be prioritized over other causes of skin discoloration. In S270 it is checked whether to continue with the operation and if so, execution continues with S220; otherwise, execution terminates.

As a non-limiting example, an image of a patient's face and a recording of the patient's voice is received. The image and the recording are then analyzed by server 130 and a plurality of signatures are generated by SGS 140 respective thereto. Based on an analysis of the signatures, an abnormal redness is identified in the patient's eye and hoarseness is identified in the patient's voice. Based on the identifiers, a search for possible diagnoses is initiated. Responsive of the search, "Scarlet fever" and "Mumps disease" may be identified as possible diagnoses. As the identifiers related to the patient's eye and hoarseness of the throat are more frequent in cases of the Scarlet fever, the Scarlet fever will be provided as the more likely result. According to one embodiment, one or more advertisements may be provided to the user based on the one or more possible diagnoses. The advertisement may be received from publisher servers (not shown) and displayed together with the one or more possible diagnoses.

Figure 3:
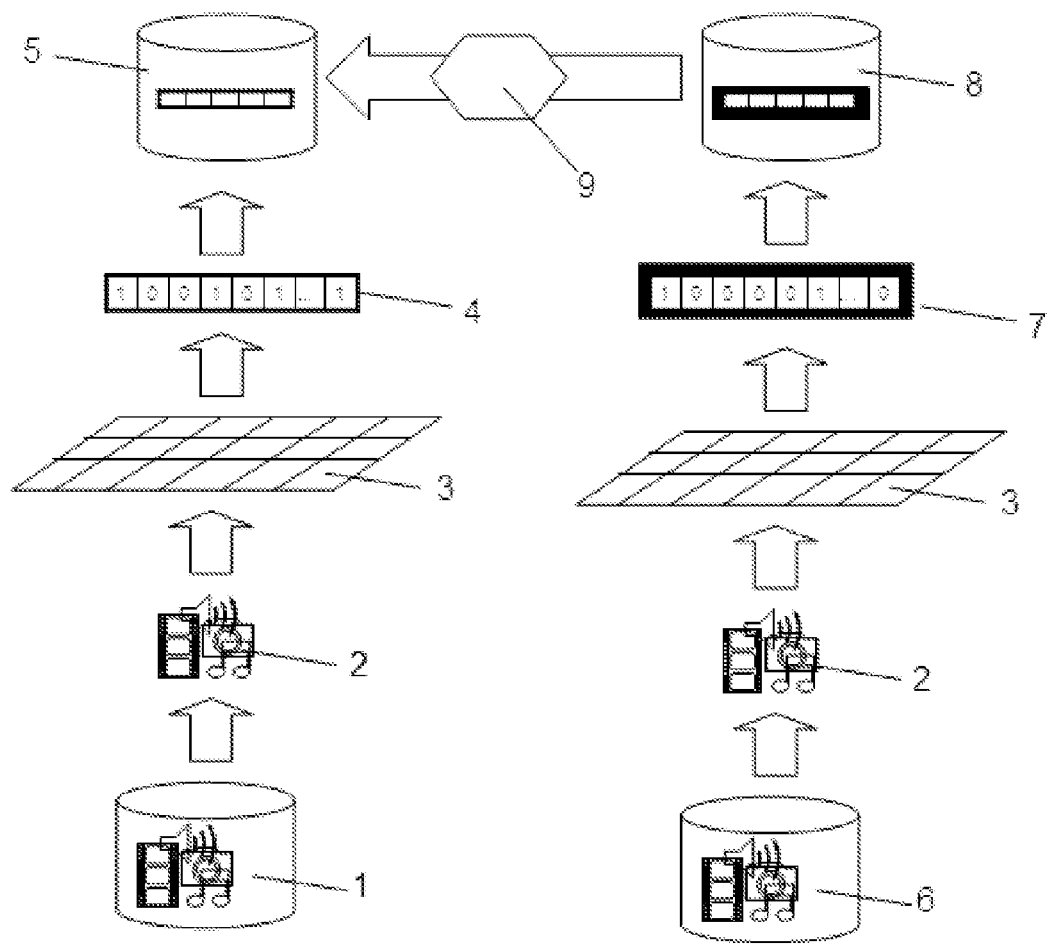
FIG. 3 is a block diagram depicting the basic flow of information in the signature generator system.
Figure 4:
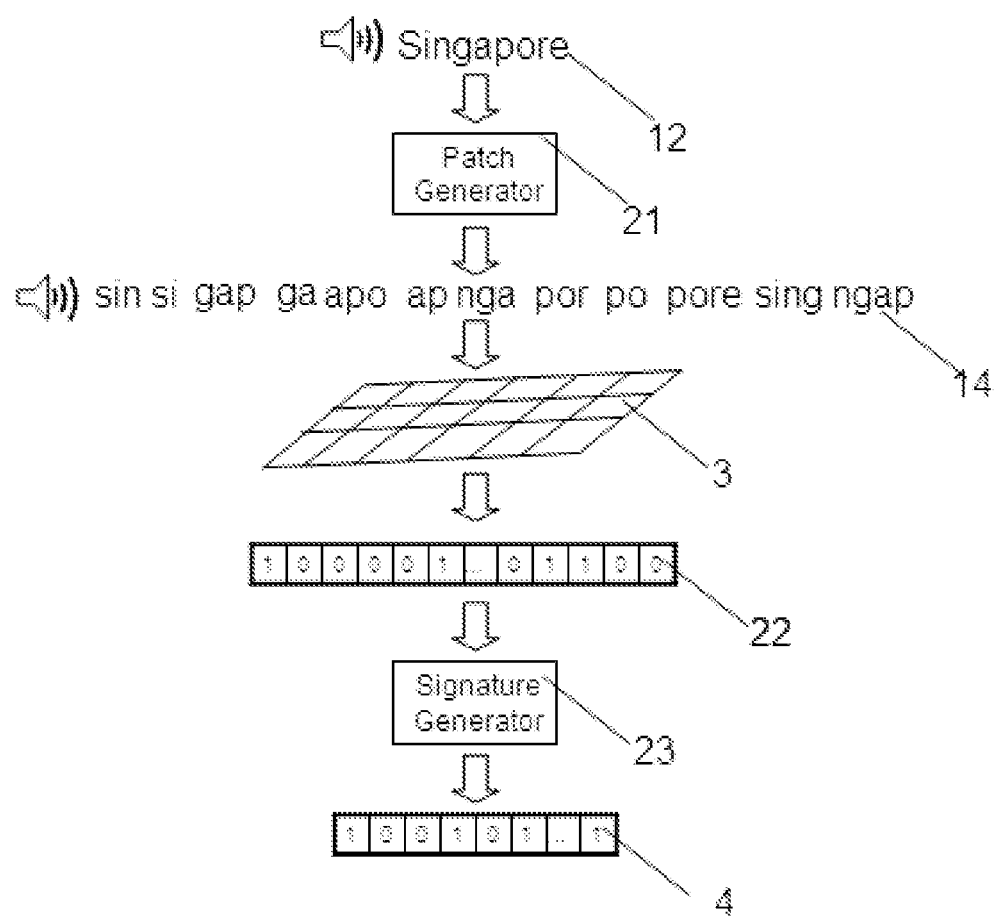
FIG. 4 is a diagram showing the flow of patches generation, response vector generation, and signature generation in a large-scale speech-to-text system.

FIGS. 3 and 4 illustrate the generation of signatures for the multimedia content elements by the SGS 140 according to one embodiment. An exemplary high-level description of the process for large scale matching is depicted in FIG. 3. In this example, the matching is for a video content.

Video content segments 2 from a Master database (DB) 6 and a Target DB 1 are processed in parallel by a large number of independent computational Cores 3 that constitute an architecture for generating the Signatures (hereinafter the "Architecture"). Further details on the computational Cores generation are provided below. The independent Cores 3 generate a database of Robust Signatures and Signatures 4 for Target content-segments 5 and a database of Robust Signatures and Signatures 7 for Master content-segments 8. An exemplary and non-limiting process of signature generation for an audio component is shown in detail in FIG. 4. Finally, Target Robust Signatures and/or Signatures are effectively matched, by a matching algorithm 9, to Master Robust Signatures and/or Signatures database to find all matches between the two databases.

To demonstrate an example of signature generation process, it is assumed, merely for the sake of simplicity and without limitation on the generality of the disclosed embodiments, that the signatures are based on a single frame, leading to certain simplification of the computational cores generation. The Matching System is extensible for signatures generation capturing the dynamics in-between the frames.

The Signatures' generation process is now described with reference to FIG. 4. The first step in the process of signatures generation from a given speech-segment is to break down the speech-segment to K patches 14 of random length P and random position within the speech segment 12. The breakdown is performed by the patch generator component 21. The value of the number of patches K, random length P and random position parameters is determined based on optimization, considering the tradeoff between accuracy rate and the number of fast matches required in the flow process of the profiling server 130 and SGS 140. Thereafter, all the K patches are injected in parallel into all computational Cores 3 to generate K response vectors 22, which are fed into a signature generator system 23 to produce a database of Robust Signatures and Signatures 4.

In order to generate Robust Signatures, i.e., Signatures that are robust to additive noise L (where L is an integer equal to or greater than 1) by the Computational Cores 3, a frame 'i' is injected into all the Cores 3. Then, Cores 3 generate two binary response vectors: $\vec{S}$ which is a Signature vector, and $\vec{RS}$ which is a Robust Signature vector.

For generation of signatures robust to additive noise, such as White-Gaussian-Noise, scratch, etc., but not robust to distortions, such as crop, shift and rotation, etc., a core $C_i=\{n_i\}$ ($1 \leq i \leq L$) may consist of a single leaky integrate-to-threshold unit (LTU) node or more nodes. The node $n_i$ equations are:

$$V_i = \sum_j w_{ij} k_j$$

$$n_i = \theta(V_i - Th_x) \qquad \qquad 1.$$

where, $\theta$ is a Heaviside step function; $w_{ij}$ is a coupling node unit (CNU) between node i and image component j (for example, grayscale value of a certain pixel j); $k_j$ is an image component 'j' (for example, grayscale value of a certain pixel j); Thx is a constant Threshold value, where x is 'S' for Signature and 'RS' for Robust Signature; and Vi is a Coupling Node Value.

The Threshold values $Th_x$ are set differently for Signature generation and for Robust Signature generation. For example, for a certain distribution of values (for the set of nodes), the thresholds for Signature ($Th_S$) and Robust Signature ($Th_{RS}$) are set apart, after optimization, according to at least one or more of the following criteria:

ii. 1: For: $V_i > Th_{RS}$ $$1 - p(V > Th_S) - 1 - (1-\epsilon)^l \gg 1$$

i.e., given that l nodes (cores) constitute a Robust Signature of a certain image I, the probability that not all of these l nodes will belong to the Signature of a same, but noisy image, Ĩ is sufficiently low (according to a system's specified accuracy).

iii. 2: $p(V_i > Th_{RS}) \approx l/L$ i.e., approximately l out of the total L nodes can be found to generate a Robust Signature according to the above definition.

iv. 3: Both Robust Signature and Signature are generated for certain frame i.

It should be understood that the generation of a signature is unidirectional, and typically yields lossless compression, where the characteristics of the compressed data are maintained but the uncompressed data cannot be reconstructed. Therefore, a signature can be used for the purpose of comparison to another signature without the need of comparison to the original data. The detailed description of the Signature generation can be found U.S. Pat. Nos. 8,326,775 and 8,312,031, assigned to common assignee, and are hereby incorporated by reference for all the useful information they contain.

A Computational Core generation is a process of definition, selection, and tuning of the parameters of the cores for a certain realization in a specific system and application. The process is based on several design considerations, such as:

(a) The Cores should be designed so as to obtain maximal independence, i.e., the projection from a signal space should generate a maximal pair-wise distance between any two cores' projections into a high-dimensional space.

(b) The Cores should be optimally designed for the type of signals, i.e., the Cores should be maximally sensitive to the spatio-temporal structure of the injected signal, for example, and in particular, sensitive to local correlations in time and space. Thus, in some cases a core represents a dynamic system, such as in state space, phase space, edge of chaos, etc., which is uniquely used herein to exploit their maximal computational power.

(c) The Cores should be optimally designed with regard to invariance to a set of signal distortions, of interest in relevant applications.

Detailed description of the Computational Core generation and the process for configuring such cores is discussed in more detail in the above-referenced U.S. Pat. No. 8,655,801, assigned to the common assignee, which is hereby incorporated by reference for all that it contains.

Figure 5:
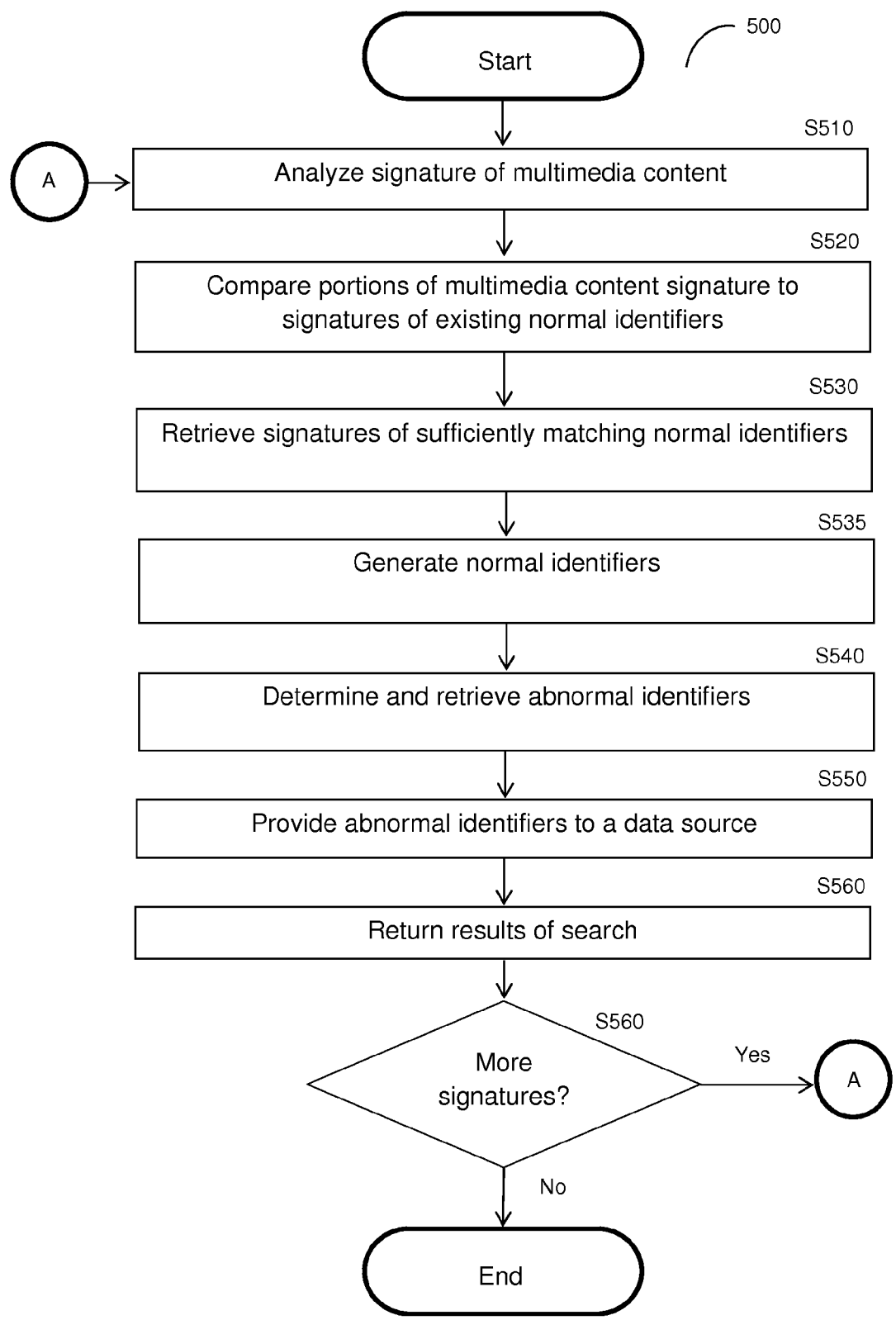
FIG. 5 is a flowchart illustrating a method for identification of possible diagnoses using identifiers according to an embodiment.

FIG. 5 is a flowchart illustrating 500 a method for identification of possible diagnoses using identifiers according to an embodiment. In S510, a signature of one or more multimedia content elements is analyzed. This analysis may yield the portions of the signature that are potentially related to one or more existing identifiers. A portion of signature may be potentially relevant if, for example, the length of the portion is above a predetermined threshold.

In S520, the potentially related portions of signatures and/or the full signature are compared to signatures of existing baseline identifiers. In an embodiment, such existing identifiers may be retrieved from a data warehouse (e.g., data warehouse 160). In another embodiment, this comparison may be conducted by performing signature matching between the portions of signatures and the signatures of normal identifiers. Signature matching is described further herein above with respect to FIG. 3.

In S530, signatures of existing baseline identifiers that demonstrated sufficient matching with the portions of signatures are retrieved. Matching may be sufficient if, e.g., the matching score is above a certain threshold, the matching score of one signature is the highest among compared signatures, and so on. Optionally in S535, one or more baseline identifiers may be generated based on the matching. In a further embodiment, generation occurs if no normal identifier demonstrated sufficient matching with the portion of the multimedia content signature.

In S540, one or more baseline identifiers is determined and retrieved. In an embodiment, baseline identifiers may be determined based on differences between the retrieved normal identifier signatures and the portions of multimedia content signatures. In S550, the baseline identifiers are provided to a data source to perform a search. In S560, the results of the search are returned. In S570, it is checked whether additional multimedia content signatures or portions thereof must be analyzed. If so, execution continues with S510; otherwise, execution terminates.

As a non-limiting example, a user provides multimedia content featuring a swollen wrist. Several portions of the signature that may be relevant to diagnosis are determined. In this example, such portions may include a hand, an arm, veins, fingers, a thumb, a patch of skin demonstrating a bump, and a discolored patch of skin. The signatures of the swollen wrist are compared to signatures in a database, and a signature related to a picture of an uninjured wrist is retrieved as a normal identifier.

The portions of the signature identifying the discoloration and disproportionately large segments of the wrist are determined to be differences. Thus, the portions of the multimedia content related to those portions of signatures are determined to be relevant abnormal identifiers. The determined abnormal identifiers are retrieved and provided to a data source. In this example, the data source performs a search based on the abnormal identifiers and determines that the abnormal identifiers are typical for sprained wrists. Thus, the results of the search indicating that the user's wrist may be sprained are returned.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform such as an additional data storage unit and a printing unit. Furthermore, a non-transitory computer readable medium is any computer readable medium except for a transitory propagating signal.

All examples and conditional language recited herein are intended for pedagogical purposes to aid the reader in understanding the principles of the invention and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

The invention claimed is:

1. A method for diagnosing a patient based on analysis of multimedia content, comprising:
   receiving at least one multimedia content element respective of the patient from a user device;
   generating at least one signature for the at least one multimedia content element by compression of the at least one multimedia element;
   generating at least one identifier respective of the at least one multimedia content element using the at least one generated signature;
   converting the at least one identifier to at least one text query;
   searching a plurality of data sources for possible diagnoses respective of the one or more identifiers using the at least one text query; and
   providing at least one possible diagnoses respective of the at least one multimedia content element to the user device.

2. The method of claim 1, further comprising:
   storing the at least one possible diagnose in a data warehouse.

3. The method of claim 1, wherein the identifiers include any one of: a visual identifier, a vocal identifier and a combination thereof.

4. The method of claim 1, further comprising:
   receiving metadata from the user device; and,
   searching through the plurality of data sources for possible diagnoses of the patient based on the at least one identifier and the received metadata.

5. The method of claim 1, further comprising:
   generating at least one signature for the at least one identifier; and
   searching through the plurality of data sources for possible diagnoses using the at least signature generated respective of the identifier.

6. The method of claim 5, wherein the generation of the at least one identifier of the patient further comprising:
   matching the generated signatures to the one or more multimedia content element of baseline identifiers; and
   identifying at least one abnormal identifier respective of the matching, wherein the at least one abnormal identifier is the generated at least one identifier.

7. The method of claim 1, wherein the multimedia content element includes at least one of: an image, graphics, a video stream, a video clip, an audio stream, an audio clip, a video frame, a photograph, images of signals, and portions thereof.

8. The method of claim 1, further comprising:
   providing an advertisement to the user device related to at least one possible diagnosis.

9. A non-transitory computer readable medium having stored thereon instructions for causing one or more processing units to execute the method according to claim 1.

10. A system for diagnosing a patient based on analysis of multimedia content, comprising:
    an interface to a network for receiving at least one multimedia content element respective of the patient from a user device;
    processing circuitry; and
    a memory communicatively connected to the processing circuitry, the memory containing instructions that, when executed by the processor, configure the system to:
    receive at least one multimedia content element respective of the patient from a user device;
    generate at least one signature for the at least one multimedia content element by compression of the at least one multimedia element;
    generate at least one identifier respective of the at least one multimedia content element using the at least one generated signature;
    convert the at least one identifier into at least one text query;
    search a plurality of data sources for possible diagnoses respective of the one or more identifiers using the at least one text query; and
    provide at least one possible diagnoses respective of the at least one multimedia content element to the user device.

11. The system of claim 10, wherein the system is communicatively connected to a signature generator system (SGS), wherein the SGS is configured to generate the at least one signature for the at least one multimedia content element.

12. The system of claim 11, wherein any of the processor and the SGS further comprises:
a plurality of computational cores configured to receive the at least one multimedia content element, each computational core of the plurality of computational cores having properties that are at least partly statistically independent from other of the plurality of computational cores, the properties are set independently of each other core.

13. The system claim 11, wherein the system is further configured to:
generate at least one signature for the at least one identifier; and
search through the plurality of data sources for possible diagnoses using the at least signature generated respective of the identifier.

14. The system of claim 13, wherein the system is further configured:
match the generated signatures to the one or more multimedia content element of normal identifiers; and
identify one or more abnormal identifiers.

15. The system of claim 10, wherein the at least one identifier includes any one of: a visual identifier, a vocal identifier, and a combination thereof.

16. The system of claim 10, wherein the interface is further configured to receive metadata elements from the user device.

17. The system of claim 10, wherein the system is further configured to search through the plurality of data sources for possible diagnoses based on the at least one identifier and the metadata.

18. The system of claim 10, wherein the multimedia content element includes at least one of: an image, graphics, a video stream, a video clip, an audio stream, an audio clip, a video frame, a photograph, images of signals, and portions thereof.

19. The system of claim 10, wherein the processor is further configured to provide an advertisement to the user device related to at least one possible diagnosis.

20. A method for diagnosing a patient based on analysis of multimedia content that includes visual and non-visual components, comprising:
receiving at least one multimedia content element respective of the patient from a user device;
generating at least one signature for the at least one multimedia content element based on its visual and non-visual components generating at least one signature for the at least one multimedia content element by compression of the at least one multimedia element;
generating at least one identifier respective of the at least one multimedia content element using the at least one generated signature;
searching a plurality of data sources for possible diagnoses respective of the one or more identifiers; and
providing at least one possible diagnoses respective of the at least one multimedia content element to the user device.

* * * * *